US012121218B2

(12) United States Patent
Guo et al.

(10) Patent No.: US 12,121,218 B2
(45) Date of Patent: Oct. 22, 2024

(54) CONFIGURING OPTICAL LIGHT PATH HAVING BEAM OVERLAP ON IMAGE SENSOR

(71) Applicant: Welch Allyn, Inc., Skaneateles Falls, NY (US)

(72) Inventors: Lei Guo, Manlius, NY (US); Joshua Hess, Moravia, NY (US); Raymond A. Lia, Auburn, NY (US); Michael T. McMahon, Syracuse, NY (US); Alan Knieriem, Baldwinsville, NY (US); Steven R. Slawson, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 447 days.

(21) Appl. No.: 17/313,669

(22) Filed: May 6, 2021

(65) Prior Publication Data

US 2021/0345866 A1 Nov. 11, 2021

Related U.S. Application Data

(60) Provisional application No. 63/022,992, filed on May 11, 2020.

(51) Int. Cl.
*A61B 1/00* (2006.01)
*A61B 1/04* (2006.01)
(Continued)

(52) U.S. Cl.
CPC .............. *A61B 1/05* (2013.01); *A61B 1/0011* (2013.01); *A61B 1/227* (2013.01); *G02B 23/04* (2013.01);
(Continued)

(58) Field of Classification Search
CPC ......... A61B 1/05; A61B 1/0011; A61B 1/227; A61B 5/0077; A61B 5/441; A61B 5/0013;
(Continued)

(56) References Cited

U.S. PATENT DOCUMENTS 3,721,170 A * 3/1973 Johnson ................. G03B 17/48
359/503
4,541,697 A 9/1985 Remijan
(Continued)

FOREIGN PATENT DOCUMENTS

CN 1180251 A 4/1998
CN 105193381 A 12/2015
(Continued)

OTHER PUBLICATIONS

Herbert Gross (Editor), Handbook of Optical Systems vol. 4—Survey of Optical Instruments, Wiley-VCH, (2008), p. 554 (Year: 2008).*

(Continued)

*Primary Examiner* — Ryan S Dunning
(74) *Attorney, Agent, or Firm* — Lee & Hayes, P.C.

(57) ABSTRACT

An accessory that is attachable to a device comprises an image sensor and a beam splitter having a first surface and a second surface. The beam splitter is configured to impinge light upon the first surface, and split the light impinging upon the first surface into at least a first beam, a second beam, and a third beam. The first beam travels from a first opening of the device to a second opening of the device along an optical path when the accessory is attached to the device, the second beam travels from the first surface to the image sensor, and the third beam travels from the second surface to the image sensor or a beam dump.

20 Claims, 8 Drawing Sheets

(51) Int. Cl.
    *A61B 1/05*         (2006.01)
    *A61B 1/227*       (2006.01)
    *A61B 3/12*         (2006.01)
    *A61B 5/00*         (2006.01)
    *G02B 23/04*       (2006.01)
    *G02B 27/10*       (2006.01)

(52) U.S. Cl.
    CPC ........ *G02B 27/106* (2013.01); *A61B 1/00195* (2013.01); *A61B 1/042* (2013.01); *A61B 3/12* (2013.01); *A61B 5/0013* (2013.01); *A61B 5/0077* (2013.01); *A61B 5/441* (2013.01)

(58) Field of Classification Search
    CPC ....... A61B 1/00195; A61B 1/042; A61B 3/12; G02B 23/04; G02B 27/106
    See application file for complete search history.

(56) References Cited

U.S. PATENT DOCUMENTS

| | | | |
|---|---|---|---|
| 5,590,148 A * | 12/1996 | Szarmes | H01S 3/081 |
| | | | 372/19 |
| 6,269,565 B1 | 8/2001 | Inbar et al. | |
| 7,364,297 B2 | 4/2008 | Goldfain et al. | |
| 7,883,505 B2 * | 2/2011 | Van Heugten | A61F 9/008 |
| | | | 606/4 |
| 8,657,976 B2 | 2/2014 | Kimura et al. | |
| 8,810,792 B2 * | 8/2014 | Dane | G02B 27/0955 |
| | | | 356/370 |
| 9,151,982 B2 | 10/2015 | Kitada et al. | |
| 9,239,416 B2 | 1/2016 | Kitada et al. | |
| 9,459,463 B2 | 10/2016 | Sharp et al. | |
| 9,751,231 B2 | 9/2017 | Kim et al. | |
| 2012/0307205 A1 | 12/2012 | Zhou | |
| 2018/0084999 A1 * | 3/2018 | Oved | A61B 3/0025 |
| 2018/0364492 A1 * | 12/2018 | Forcht | G02B 21/16 |
| 2022/0155574 A1 * | 5/2022 | Fisch | G02B 21/125 |

FOREIGN PATENT DOCUMENTS

| | | |
|---|---|---|
| JP | S63284516 A | 11/1988 |
| JP | 2017067664 A | 4/2017 |
| JP | 2017102479 A | 6/2017 |
| KR | 20080052825 A | 6/2008 |
| WO | WO9103201 A1 | 3/1991 |

OTHER PUBLICATIONS

Newport Corporation website for broadband plate dielectric beamsplitter technical specs from Wayback Machine (Apr. 13, 2019) (Year: 2019).*
Extended European Search Report mailed Sep. 30, 2021 for European Patent Application No. 21172473.7, 9 pages.
European Office Action mailed Jul. 20, 2022 for European Patent Application No. 21172473.7, a foreign counterpart to U.S. Appl. No. 17/313,669, 5 pages.

* cited by examiner

CONFIGURING OPTICAL LIGHT PATH HAVING BEAM OVERLAP ON IMAGE SENSOR

CROSS-REFERENCE TO RELATED APPLICATION

This application is a U.S. Nonprovisional Application of, and claims priority to, U.S. Provisional Application No. 63/022,992, filed May 11, 2020, the entire disclosure of which is incorporated herein by reference.

FIELD OF THE INVENTION

The present disclosure relates to systems and methods for configuring an optical light path and, in particular, to systems and methods for configuring components within a device to selectively direct light to an image sensor or other type of detector or sensor.

BACKGROUND OF THE INVENTION

Visual observation is a common technique for healthcare providers to determine a patient's health status. Many tools exist to assist healthcare providers with visual observations of patients. For example, an otoscope assists healthcare providers with viewing inside of a patient's ear, such as during regular health check-ups and/or to investigate ear symptoms. An ophthalmoscope assists healthcare providers with viewing inside of the fundus of a patient's eye, such as part of an eye exam and/or a routine physical exam. A dermatoscope assists healthcare providers with viewing skin lesions without the interference of skin surface reflections, which is useful in distinguishing between benign and malignant lesions on a patient's skin. These are but a few examples of tools that may assist a healthcare provider with visual observations of a patient.

Conventional tools that assist healthcare providers with visual observations, such as the ones described above, include a channel or opening that allows light to pass through the device, and may alter the light in some way (e.g., using lenses) based on the type of visual observation to be conducted using the device. In some cases, such tools may alternatively or additionally include a digital imaging component that allows the healthcare provider to capture images and/or video of an exam, which may be viewed in real time, and/or may be stored for review at a later time. However, tools that incorporate a digital imaging component block the opening that allows light to pass through the device during a traditional examination in order to capture light for the creation of digital images. Additionally, display devices that provide real time viewing (e.g., during a patient examination) using such tools are often disposed in a remote location from the device (e.g., on a computer monitor on a desk in the exam room), which causes a disruption in the workflow of the healthcare provider conducting the exam. For example, a healthcare provider may have to take their attention from the tool performing the visual observation to look at a monitor of the images being captured by the digital imaging component on a computer monitor, which may inhibit the healthcare provider's ability to make precise movements with the tool during the exam.

Examples of the present disclosure are directed toward overcoming the deficiencies described above.

SUMMARY

In an example of the present disclosure, a device comprises a housing defining an internal space that includes a first opening and a second opening. The device may also include an optics assembly disposed within the internal space, where the optics assembly is configured to receive light, via the first opening, from a source external to the housing, and direct the light to pass, through the housing, to the second opening along an optical path. The device may also include an accessory removably connectable to the housing. The accessory may comprise an image sensor and a beam splitter having a first surface and a second surface, such that when the accessory is removably connected to the housing, the light impinges upon the first surface. Additionally, when the accessory is removably connected to the housing, the beam splitter splits the light impinging upon the first surface into at least a first beam, a second beam, and a third beam. The first beam travels from the first opening to the second opening along the optical path, the second beam travels from the first surface to the image sensor, and the third beam travels from the second surface to the image sensor or a beam dump.

In another example of the present disclosure, an accessory attachable to a housing of a medical device comprises an image sensor and a beam splitter having a first surface and a second surface. When the accessory is attached to the housing of the medical device, the first surface of the beam splitter is configured to receive light via a first opening of the housing, and the beam splitter is configured to split the light into at least a first beam, a second beam, and a third beam. The first beam travels from the first surface to a second opening of the housing along a first optical path extending from the first surface to the second opening. The second beam travels from the first surface to the image sensor along a second optical path. The third beam travels from the first surface to the image sensor or a beam dump along a third optical path extending from the first surface to the image sensor or the beam dump via the second surface.

In a further example of the present disclosure, a method of manufacturing an accessory for a medical device includes providing a coupling mechanism for removably attaching the accessory to the medical device, providing an image sensor for converting light into an image or a video, and providing a beam splitter. When the accessory is attached to the housing of the medical device, the first surface of the beam splitter is configured to receive light via a first opening of the housing, and the beam splitter is configured to split the light into a first beam, a second beam, and a third beam. The first beam travels from the first surface to a second opening of the housing along a first optical path extending from the first surface to the second opening when the accessory is attached to the medical device via the coupling mechanism. The second beam travels from the first surface to the image sensor along a second optical path. The third beam travels from the first surface to the image sensor or a beam dump along a third optical path extending from the first surface to the image sensor or the beam dump via the second surface.

DETAILED DESCRIPTION

Figure 1:
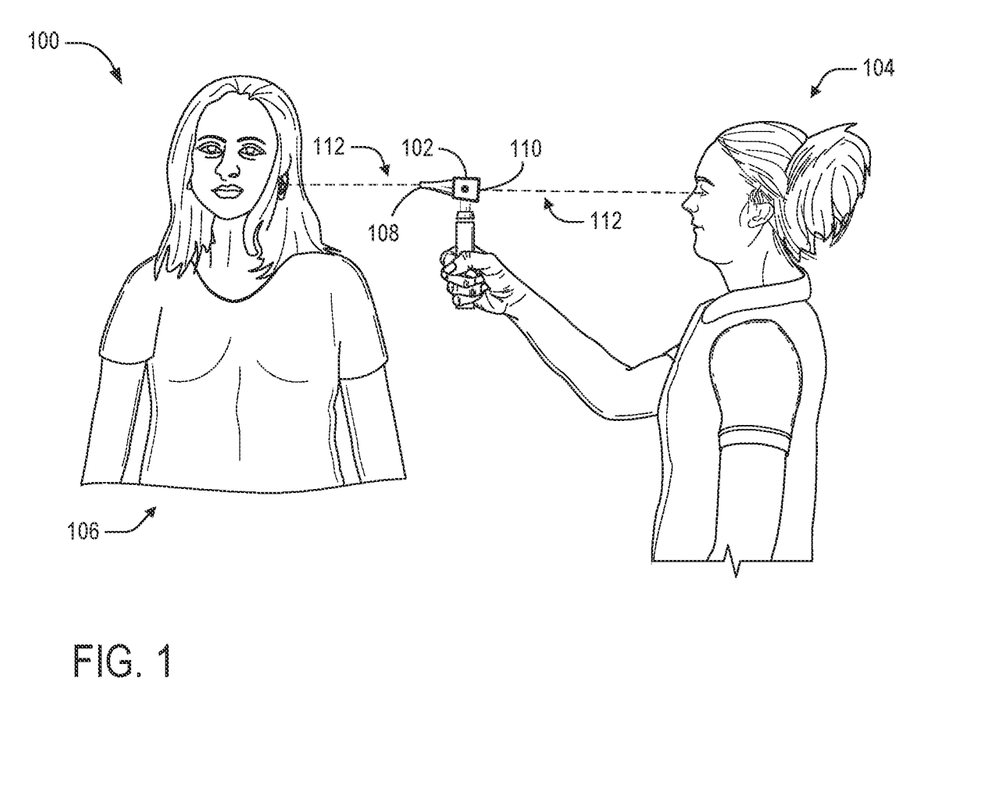
FIG. 1 illustrates a visual observation system according to an example of the present disclosure.

FIG. 1 illustrates a visual observation system 100 of the present disclosure including a device 102 configured to enable a healthcare provider 104 (or other user) to perform a visual observation of a patient 106 (or other user). In the illustrated example, the device 102 is an otoscope configured to assist the healthcare provider 104 with viewing inside of an ear of the patient 106. It is understood that the depiction of the device 102 (e.g., an otoscope) is merely exemplary. In examples, the concepts described herein may be applicable to any other medical device that assists the healthcare provider 104 with visual observations of the patient 106. Such devices may include, for example, probes, ophthalmoscopes, dermatoscopes, endoscopes, and the like. Additionally, while examples are generally described in relation to a handheld device, examples are considered in which the device 102 assists the healthcare provider 104 to perform visual observations of the patient 106 without being held by the healthcare provider 104, such as worn on a head of the healthcare provider 106 (e.g., a binocular ophthalmoscope), mounted to and/or placed upon a surface, held and/or worn by the patient 106, and so forth.

In examples, the device 102 includes a first end 108 and a second end 110, which may be opposite one another on the device 102. The first end 108 may be oriented towards (e.g., facing) the patient 106 and the second end 110 may be oriented towards (e.g., facing) the healthcare provider 104 during an examination of the patient 106. In such an orientation, light 112 reflected by at least a portion of the patient 106 enters the first end 108 of the device 102. The device 102 may include lenses, mirrors, beam splitters, or other light manipulating components tailored to assist the healthcare provider 104 with a particular type of visual observation of the patient 106. As described herein, different types of devices may have different interior components to manipulate the light 112 based on a type of exam that the device 102 is intended to assist with. At least a portion of the light 112 passes through the device 102, along with light manipulation components included in the device 102, and out of the second end 110 of the device 102 to an eye of the healthcare provider 104, enabling the healthcare provider 104 to make visual observations of the patient 106. Although not explicitly pictured in the visual observation system 100, the device 102 may be configured to have an accessory attached that captures a portion of the light 112 to generate images and/or video while the healthcare provider 104 performs the exam of the patient 106, without impeding the healthcare provider 104 from viewing the portion of the patient in the manner described in relation to FIG. 1.

Figure 2:
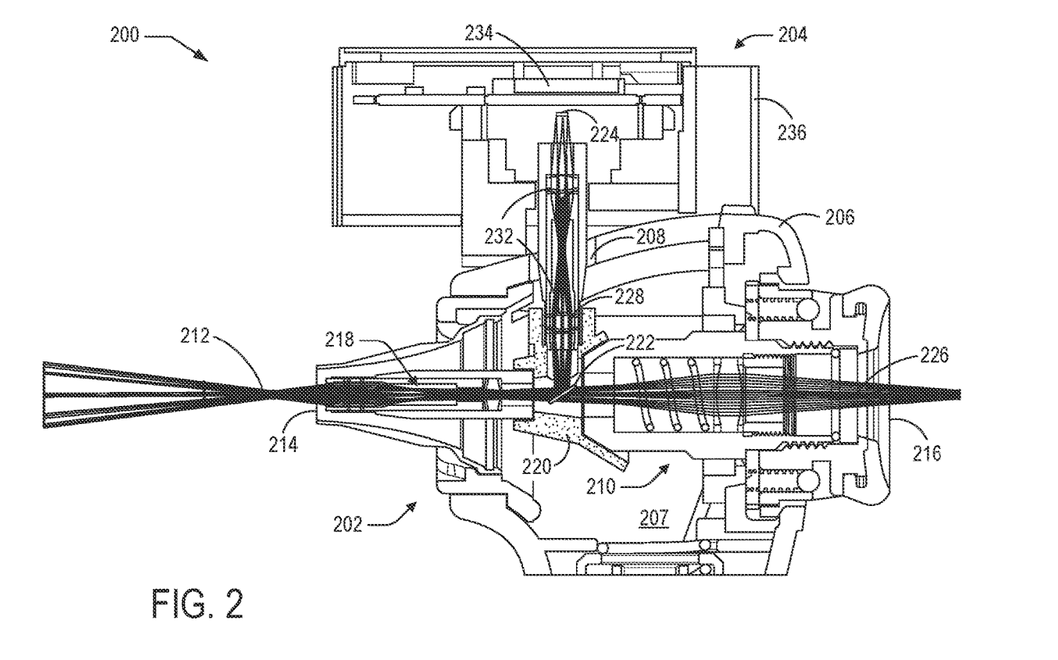
FIG. 2 illustrates a cross-sectional view of a portion of an example visual observation tool of the present disclosure.

FIG. 2 illustrates a cross-sectional view of a portion of an example visual observation tool 200 of the present disclosure. In this example, the visual observation tool 200 comprises an otoscope 202, such as the otoscope described in relation to FIG. 1. Additionally, the visual observation tool 200 comprises an accessory 204 that, in some examples, is removably connectable to a housing 206 of the otoscope 202. For instance, the housing 206 may include an opening 208 that permits a portion of the accessory 204 to enter the housing 206 of the otoscope 202. The housing 206 generally defines an internal space 207 which may contain an optics assembly 210 comprising components such as a light, optical fibers, lenses, mirrors, and the like. In such examples, at least a portion of the accessory 204 may be disposed within the internal space 207 when the accessory 204 is removably connected to the housing 206.

In some examples, the optics assembly 210 receives light 212 via a first opening (e.g., the first end 108 of FIG. 1) 214 from a source external to the housing 206. The optics assembly 210 directs the light 212 to pass through the housing 206 to a second opening 216 (e.g., the second end 110 of FIG. 1) along an optical path 218. The optical path 218 permits the light 212 to pass from the first opening 214 of the otoscope 202 to the second opening 216 of the otoscope 202, similar to the light 112 passing through the device 102 in relation to FIG. 1. For instance, the light 212 may be reflected off of a portion of the patient 106 of FIG. 1 during an exam by the healthcare provider 104 of the patient 106. As the light 212 traverses the optical path 218 through the otoscope 202, the healthcare provider 104 is able to view a portion of the patient 106, such as an interior of an ear of the patient 106, from the second opening 216 of the otoscope 202.

As mentioned above, the visual observation tool 200 may also include an accessory 204 that is removably connected to the housing 206. The accessory 204 may be connected to the housing 206 by a coupling mechanism such as a threaded fastener, a buckle, a clamp, a clasp, a hook and loop fastener, a latch, a pin, a snap fastener, or the like. When the accessory 204 is connected to the otoscope 202, a portion 220 (indicated by patterned fill) of the accessory 204 that enters the otoscope 202 may intercept the optical path 218. In examples, the accessory 204 includes a beam splitter 222 disposed in the portion 220 of the accessory 204 that intercepts the optical path 218. The light 212 may impinge upon (e.g., strike the surface of) the beam splitter 222 as the light 212 travels along the optical path 218. Based on a shape, configuration, surface treatment, and other factors discussed in more detail in relation to FIGS. 4 and 5, the beam splitter 222 may direct portions of the light 212 to continue along the optical path 218, be directed to an image sensor 224 included in the accessory 204, and/or be directed to a beam dump (not shown). Although described in relation to an image sensor herein, other sensor types are also contemplated and may be used in place of or in addition to the image sensors described. For example, the visual observation tool 200 (and/or other devices described herein) may include a multispectral sensor that records signals, such as spectral information, that are used in assisting with a diagnosis of the patient 106. The multispectral sensor may measure reflected energy within several specific sections, or bands, of the electromagnetic spectrum to generate a multispectral image. Other examples of sensor types are also considered.

For instance, the beam splitter 222 may split the light 212 such that a first beam 226 travels from the first opening 214 to the second opening 216 along the optical path 218 for manual viewing by the healthcare provider 106. Additionally, in some cases, the beam splitter 222 may split the light 212 such that a second beam 228 travels from the beam splitter 222 to the image sensor 224 to form an image and/or a video in real time corresponding to what the healthcare provider 106 is manually viewing through the otoscope 202. Further, in some examples, the beam splitter 222 may split the light 212 such that a third beam (not shown) also travels from the beam splitter 222 to the image sensor 224 to form an image and/or a video with the second beam 228, where the third beam is used to eliminate visual effects such as ghosting and/or chromatic aberration in the image or video. In some cases, the beam splitter 222 may split the light 212 such that the third beam travels from the beam splitter 222 to a beam dump to reduce reflections and/or scattering of light in the internal space 207. For instance, a beam dump is an optical element designed to absorb a beam of light. In examples, one or more lenses 232 may be disposed between the beam splitter 222 and the image sensor 224 to focus and/or divert the second beam 228 and/or the third beam as desired based on an application of the accessory 204.

In some examples, the accessory 204 may include components such as a camera or other like imaging device configured to capture digital or other like images of the patient 106 adjacent the first opening 214 based on the second beam 228 and/or the third beam directed to the image sensor 224. The accessory 204 may also include a controller 234 comprising an image processor configured to receive signals and/or other inputs from the image sensor 224, and use the signals from the image sensor 224 to form a visual image or video of the patient 106 based on the signal. For example, the controller 234 may include a digital storage component, in communication with the image sensor 224, that is configured to store an image or a video captured by the image sensor 224. Such a visual image or video may be provided on a display 236 of the accessory 204, and/or may be transmitted by the controller 234 to a remote display or storage for later viewing. For instance, the controller 234 may include a digital transfer component that is configured to transfer the image or the video from the digital storage component to a remote computing device wirelessly via BLUETOOTH®, WIFI®, or other like means. In some examples, the accessory 204 may include one or more ports, connectors, terminals, and/or other like connection devices configured to enable communication between the digital transfer component and one or more separate devices. In addition to the image processor, digital storage component, and digital transfer described above, the controller 234 may comprise memory, additional processors (e.g., a microprocessor or other components generally associated with or included in a computer, a tablet, a mobile phone, or other computing device), and/or other known controller components to facilitate the functionality described herein.

As described above, the accessory 204 may include a display 236 connected to the image processor of the controller 234. The display 236 may comprise, for example, a liquid crystal display (LCD) screen, a light emitting diode (LED) display, a digital read-out, an interactive touchscreen, and/or any other like components configured to communicate information to the user. The display 236 may be configured to communicate such information, including images and/or video based on the second beam 228 and/or the third beam received by the image sensor 224, substantially instantaneously and/or substantially continuously depending on the mode of operation of the accessory 204.

Figure 3:
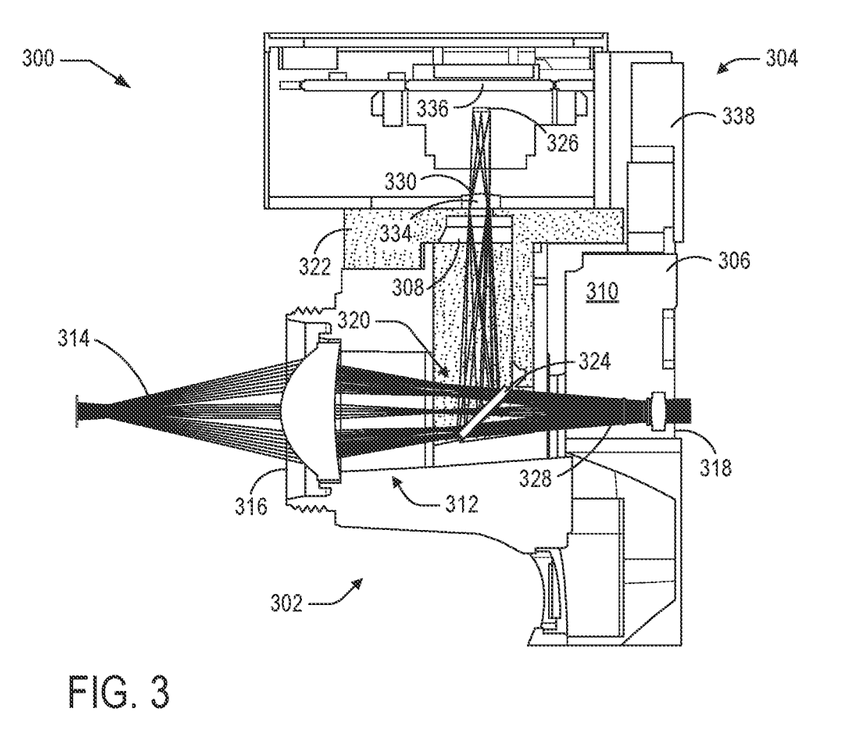
FIG. 3 illustrates a cross-sectional view of a portion of another example visual observation tool of the present disclosure.

FIG. 3 illustrates a cross-sectional view of a portion of another example visual observation tool 300 of the present disclosure. In this example, the visual observation tool 300 comprises an ophthalmoscope 302, which the healthcare provider 104 may use to view inside of a fundus of an eye of the patient 106, such as part of an eye exam and/or a routine physical exam. Additionally, the visual observation tool 300 comprises an accessory 304 that, in some examples, is removably connectable to a housing 306 of the ophthalmoscope 302. For instance, the housing 306 may include an opening 308 that permits a portion of the accessory 304 to enter inside of the housing 306 of the ophthalmoscope 302. The housing 306 generally defines an internal space 310 which may contain an optics assembly 312 comprising components such as a light, optical fibers, lenses, mirrors, and the like, similar to the optics assembly 210 described in relation to FIG. 2.

Similar to the discussion above with regard to FIG. 2, the optics assembly 312 receives light 314 via a first opening 316 (e.g., the first end 108 of FIG. 1) from a source external to the housing 306. The optics assembly 312 directs the light 314 to pass through the housing 306 to a second opening 318 (e.g., the second end 110 of FIG. 1) along an optical path 320. The optical path 320 permits the light 314 to pass from the first opening 316 of the ophthalmoscope 302 to the second opening 318 of the ophthalmoscope 302, similar to the discussion of the light 112 passing through the device 102 in relation to FIG. 1. For instance, the light 314 may be reflected off of a portion of the patient 106 of FIG. 1 during an exam by the healthcare provider 104 of the patient 106. As the light 314 traverses the optical path 320 through the ophthalmoscope 302, the healthcare provider 104 is able to view a portion of the patient 106, such as a fundus of an eye of the patient 106, from the second opening 318 of the ophthalmoscope 302.

As mentioned above, the visual observation tool 300 may also include an accessory 304 that is removably connected to the housing 306. The accessory 304 may be connected to the housing 306 by a coupling mechanism as described above. When the accessory 304 is connected to the ophthalmoscope 302, a portion 322 (indicated by patterned fill) of the accessory 304 that enters the ophthalmoscope 302 may intercept the optical path 320. In examples, the accessory 304 includes a beam splitter 324 disposed in the portion 322 of the accessory 304 that intercepts the optical path 320. The light 314 may impinge upon (e.g., strike the surface of) the beam splitter 324 as the light 314 travels along the optical path 320. Based on a shape, configuration, surface treatment, and other factors discussed in more detail in relation to FIGS. 4 and 5, the beam splitter 324 may direct portions of the light 314 to continue along the optical path 320, be directed to an image sensor 326 included in the accessory 304, and/or be directed to a beam dump.

For instance, the beam splitter 324 may split the light 314 such that a first beam 328 travels from the first opening 316 to the second opening 318 along the optical path 320 for manual viewing by the healthcare provider 106. Additionally, in some cases, the beam splitter 324 may split the light 314 such that a second beam 330 travels from the beam splitter 324 to the image sensor 326 to form an image and/or a video in real time corresponding to what the healthcare provider 106 is manually viewing through the ophthalmoscope 302. Further, in some examples, the beam splitter 326 may split the light 314 such that a third beam (not shown) also travels from the beam splitter 324 to the image sensor 326 to form an image and/or a video with the second beam 330, where the third beam is used to eliminate visual effects such as ghosting and/or chromatic aberration in the image or video. In some cases, the beam splitter 324 may split the light 314 such that the third beam travels from the beam splitter 324 to a beam dump (not shown) to reduce reflections and/or scattering of light in the internal space 310. In examples, one or more lenses 334 may be disposed between the beam splitter 324 and the image sensor 326 to focus and/or divert the second beam 330 and/or the third beam as desired based on an application of the accessory 304.

In some examples, the accessory 304 may include components such as a camera or other like imaging device. The camera may be configured to capture digital or other like images of the patient 106 adjacent the first opening 316 based on the second beam 330 and/or the third beam directed to the image sensor 326. The accessory 304 may also include a controller 336 comprising an image processor configured to receive signals and/or other inputs from the image sensor 326, and use the signals from the image sensor 326 to form a visual image or video of the patient 106 based on the signal. For example, the controller 336 may include a digital storage component, in communication with the image sensor 326, that is configured to store an image or a video captured by the image sensor 326. Such a visual image or video may be provided on a display 338 of the accessory 304, and/or may be transmitted by the controller 336 to a remote display or storage for later viewing. The display 338 may have similar functionalities and capabilities as the display 236 of FIG. 1. In examples, the controller 336 may include a digital transfer component that is configured to transfer the image or the video from the digital storage component to a remote computing device wirelessly via BLUETOOTH®, WIFI®, or other like means. In some examples, the accessory 304 may include one or more ports, connectors, terminals, and/or other like connection devices configured to enable communication between the digital transfer component and one or more separate devices. In addition to the image processor, digital storage component, and digital transfer described above, the controller 336 may comprise memory, additional processors (e.g., a microprocessor or other components generally associated with or included in a computer, a tablet, a mobile phone, or other computing device), and/or other known controller components to facilitate the functionality described herein.

Figure 4:
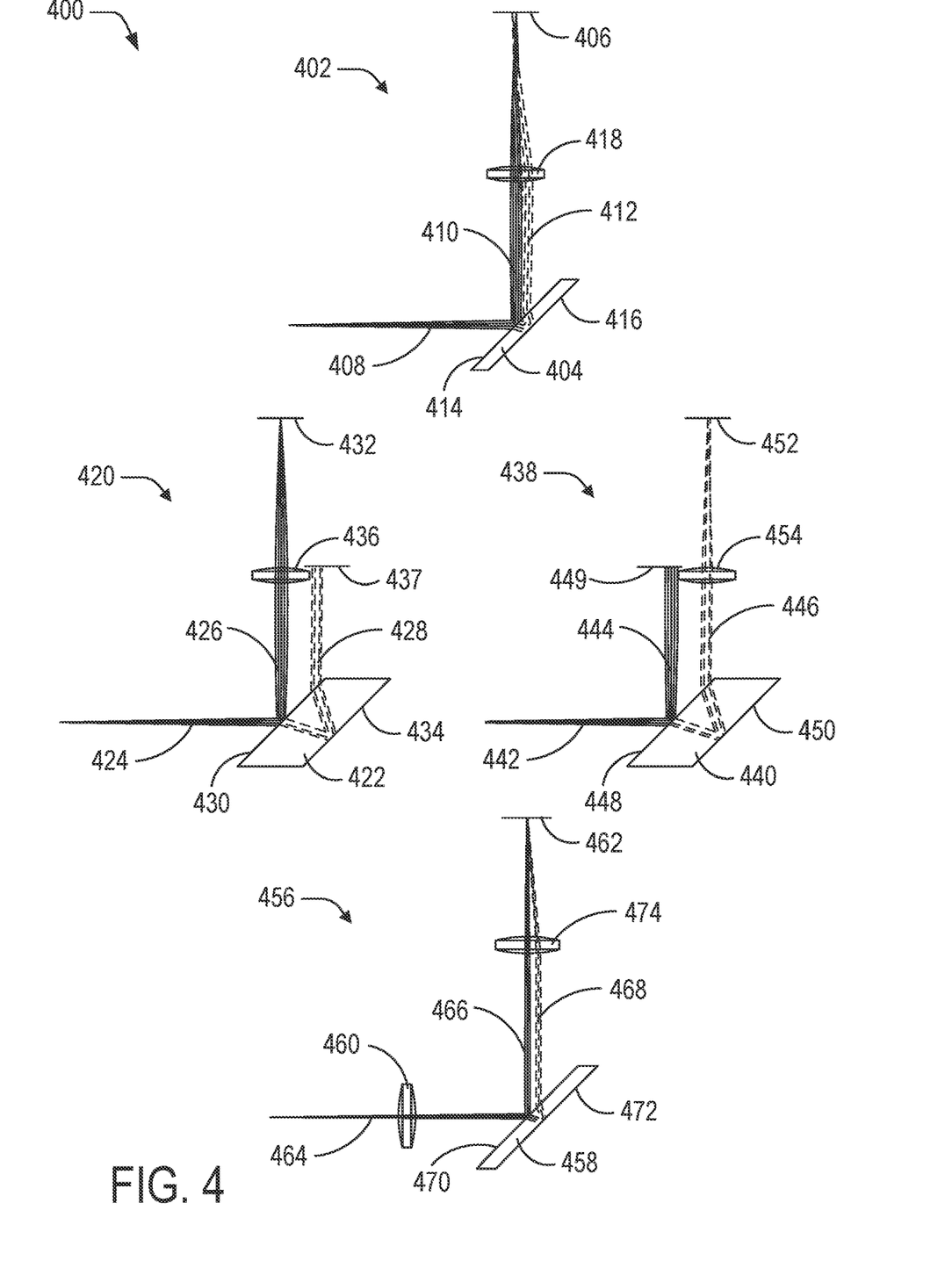
FIG. 4 is a schematic illustration of different beam splitter configurations that may be used in a visual observation tool in accordance with examples of the present disclosure.

FIG. 4 is a schematic illustration 400 of different beam splitter configurations that may be used in a visual observation tool in accordance with examples of the present disclosure. The schematic illustration 400 includes beam splitter configurations in which the beam splitter is a parallel plate having two surfaces that are substantially parallel to one another. The beam splitters in the schematic illustration 400 may be coated or uncoated on either of the substantially parallel surfaces. The thickness of the beam splitters in the schematic illustration 400 may range from approximately 1 micron to approximately 50 millimeters. In further examples, the thickness of the beam splitter may be greater than or less than those noted above. Any of the beam splitter configurations described in relation to FIG. 4 and FIG. 5 may be polarized or unpolarized. In the examples illustrated in FIG. 4 and FIG. 5, beams of light (e.g., the first beam 226 and the first beam 328) that traverse an optical path (e.g., the optical path 218 and the optical path 320) are not illustrated for clarity.

A configuration 402 illustrates a beam splitter 404 that is a relatively thin (e.g., 0.1 micron to 10 millimeters) parallel plate, which is configured for a finite conjugate application. A finite conjugate application is a configuration in which an object (e.g., a portion of the patient 106 being viewed by the healthcare provider 104 using the device 102) or intermediate image plane is located at a finite distance from the beam splitter 404. In a finite conjugate application, light is reflected from both the front and rear surface onto an image sensor 406. For example, light 408 impinging upon the beam splitter 404 is split into a first beam 410 and a second beam 412. The first beam 410 is reflected from a first surface 414 of the beam splitter 404 to the image sensor 406, and the second beam 412 is reflected from the first surface 414 of the beam splitter, to a second surface 416 of the beam splitter, and then to the image sensor 406. A lens 418 may be configured between the beam splitter 414 and the image sensor 406 to focus the first beam 410 and the second beam 412 on the image sensor 406.

In some cases, the beam splitter 404 causes chromatic aberration and/or ghost images on the image sensor 406 due to image shift between light reflected from both surfaces of the beam splitter 404. Depending on a thickness of the beam splitter 404 and image shift relative to the image sensor 406, image resolution may be compromised in such scenarios. However, ghosting and chromatic aberration may be resolved by utilizing a relatively thin (e.g., 0.1 micron to 1 millimeter) beam splitter, such as a pellicle beam splitter.

A configuration 420 illustrates a beam splitter 422 that is a relatively thick (e.g., 5 millimeters to 50 millimeters) parallel plate, which is also configured for a finite conjugate application. Similar to the discussion above, light 424 impinging upon the beam splitter 422 is split into a first beam 426 and a second beam 428. The first beam 426 is reflected from a first surface 430 of the beam splitter 422 to an image sensor 432. However, the second beam 428 is reflected from the first surface 430 of the beam splitter, to a second surface 434 of the beam splitter, and then away from a lens 436 and the image sensor 432, such as to a beam dump 437. Directing the second beam 428 away from the lens 436 and the image sensor 432 may reduce reflections and/or scattering of light inside of the device or accessory in which the beam splitter 422 and the image sensor 432 are housed.

A configuration 438 illustrates a beam splitter 440 that is a relatively thick (e.g., 5 millimeters to 50 millimeters) parallel plate, which is also configured for a finite conjugate application. Similar to the discussion above, light 442 impinging upon the beam splitter 440 is split into a first beam 444 and a second beam 446. The first beam 444 in this example is reflected from a first surface 448 of the beam splitter 440 to a beam dump 449. Additionally, the second beam 446 is reflected from the first surface 448 of the beam splitter 440, to a second surface 450 of the beam splitter, and then towards an image sensor 452 by way of a lens 454. Directing the first beam 444 away from the lens 454 and the image sensor 452 may reduce reflections and/or scattering of light inside of the device or accessory in which the beam splitter 440 and the image sensor 452 are housed.

A configuration 456 illustrates a beam splitter 458 that is a parallel plate configured for an infinite conjugate application. An infinite conjugate application is a configuration in which an object (e.g., a portion of the patient 106 being viewed by the healthcare provider 104 using the device 102) is located at an infinite distance from the beam splitter 458. If an intermediate image plane is present in the infinite conjugate application, a collimating lens 460 is configured to move a virtual image of the object to infinity. In an infinite conjugate application, light is reflected from both the front and rear surface of the beam splitter 458 onto an image sensor 462. For example, light 464 impinging upon the beam splitter 458 is split into a first beam 466 and a second beam 468. The first beam 466 is reflected from a first surface 470 of the beam splitter 458 to the image sensor 462, and the second beam 468 is reflected from the first surface 470 of the beam splitter, to a second surface 472 of the beam splitter, and then to the image sensor 462. A lens 474 may be configured between the beam splitter 458 and the image sensor 462 to focus the first beam 466 and the second beam 468 on the image sensor 462.

Unlike the configuration 402 that included a finite conjugate application, the configuration 456 the first beam 466 and the second beam 468 converge and overlap on the image sensor 462. Consequently, there is no image shift between the first beam 466 and the second beam 468, and the thickness of the beam splitter 458 does not affect the image quality of the image created by the image sensor 462. Thus, effects such as chromatic aberration and/or ghost images may be avoided in the configuration 456.

Figure 5:
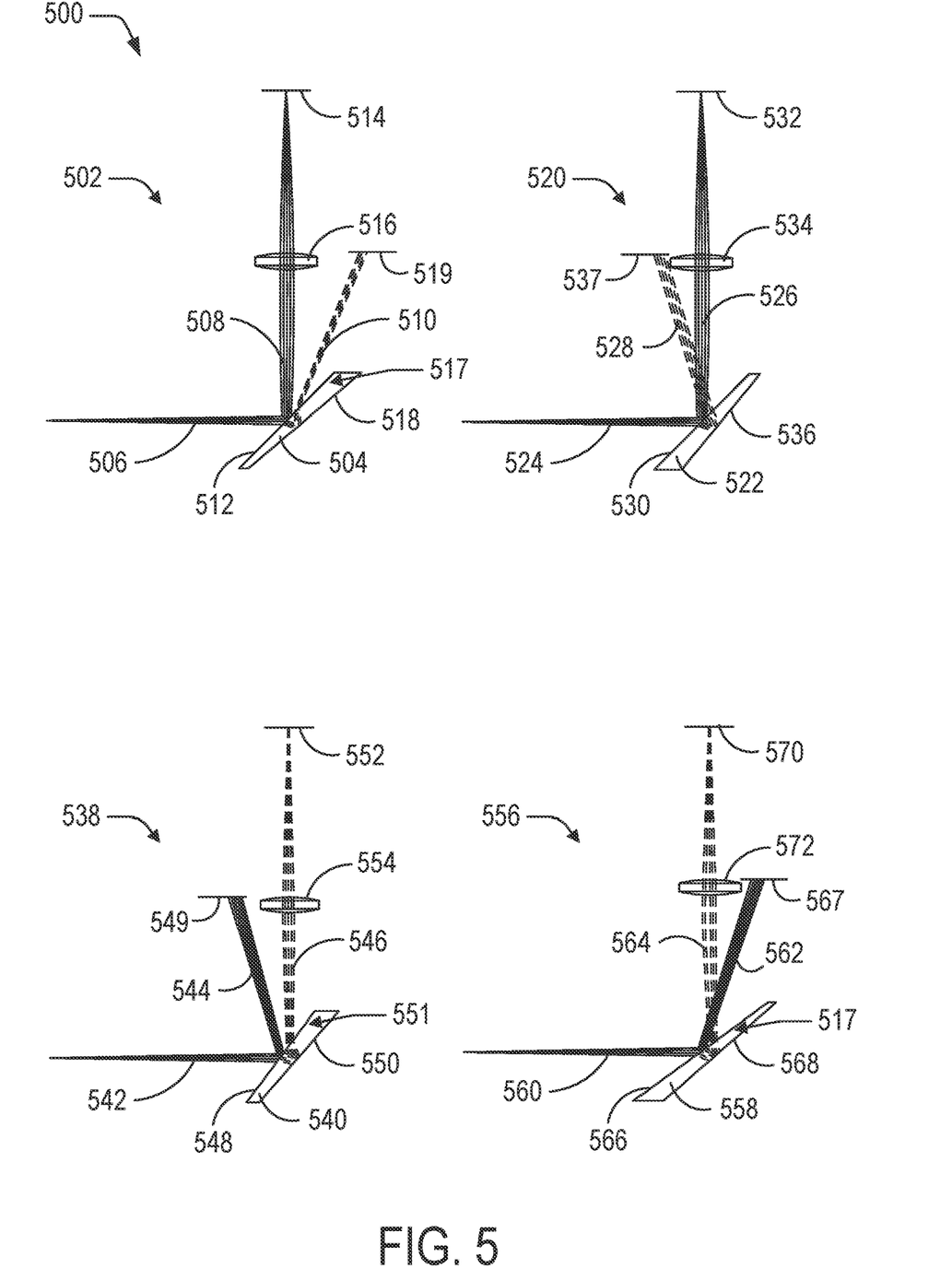
FIG. 5 is a schematic illustration of additional beam splitter configurations that may be used in a visual observation tool in accordance with examples of the present disclosure.

FIG. 5 is a schematic illustration 500 of additional beam splitter configurations that may be used in a visual observation tool in accordance with examples of the present disclosure. The schematic illustration 500 includes beam splitter configurations in which the beam splitter is a wedge plate having two surfaces that are at an angle greater than 0 degrees and less than 180 degrees relative to one another (e.g., not parallel to one another). The beam splitters in the schematic illustration 500 may be coated or uncoated on either of the angled surfaces. Generally, a wedged plate is used to reflect light from either a front surface or a rear surface onto an image sensor. The light from the other surface (e.g., the surface that does not reflect light to the image sensor) will miss a lens between the beam splitter and the image sensor, and will be terminated by a beam dump. Using a wedge plate as a beam splitter may change the boresight of the healthcare provider 104 when performing manual viewing using the device 102. However, the boresight alterations may be corrected with additional optical components (such as a wedge substrate) after the beam passes the beam splitter and before the beam leaves the device 102 to be viewed by the healthcare provider 104.

For example, a configuration 502 illustrates a beam splitter 504 that is configured as a wedge plate. Light 506 impinging upon the beam splitter 504 is split into a first beam 508 and a second beam 510. The first beam 508 in this example is reflected from a first surface 512 of the beam splitter 504 to an image sensor 514 via a lens 516. The second beam 510 is reflected from the first surface 512 of the beam splitter 504, to a second surface 518 of the beam splitter, to a reverse side 517 of the first surface 518 of the beam splitter. The reverse side 517 of the first surface 518 of the beam splitter 504 directs the second beam 510 to a beam dump 519. The beam dump 519 in the configuration 502 may be on a different side of the beam splitter 504 from which the light 506 originated. Directing the second beam 510 away from the lens 516 and the image sensor 514 may reduce reflections and/or scattering of light inside of the device or accessory in which the beam splitter 504 and the image sensor 514 are housed.

A configuration 520 illustrates a beam splitter 522 that is also configured as a wedge plate. Light 524 impinging upon the beam splitter 522 is split into a first beam 526 and a second beam 528. The first beam 526 in this example is reflected from a first surface 530 of the beam splitter 522 to an image sensor 532 via a lens 534. The second beam 528 is reflected from the first surface 530 of the beam splitter 522, to a second surface 536 of the beam splitter, and then to a beam dump 537. The beam dump in the configuration 520 may be on a same side of the beam splitter 522 from which the light 534 originated. Similar to the discussion above, directing the second beam 528 away from the lens 534 and the image sensor 532 may reduce reflections and/or scattering of light inside of the device or accessory in which the beam splitter 522 and the image sensor 532 are housed.

Additionally, a configuration 538 illustrates a beam splitter 540 that is configured as a wedge plate. Light 542 impinging upon the beam splitter 540 is split into a first beam 544 and a second beam 546. The first beam 544 in this example is reflected from a first surface 548 of the beam splitter 540 to a beam dump 549 on a same side of the beam splitter 540 from which the light 542 originated. The second beam 546 is reflected from the first surface 548 of the beam splitter 540, to a second surface 550 of the beam splitter, to a reverse side 551 of the first surface 548 of the beam splitter. The reverse side 551 of the first surface 548 of the beam splitter 540 directs the second beam 546 to an image sensor 552 via a lens 554. Similar to the discussion above, directing the first beam 544 away from the lens 554 and the image sensor 552 may reduce reflections and/or scattering of light inside of the device or accessory in which the beam splitter 540 and the image sensor 552 are housed.

A configuration 556 illustrates a beam splitter 558 that is also configured as a wedge plate. Light 560 impinging upon the beam splitter 558 is split into a first beam 562 and a second beam 564. The first beam 562 in this example is reflected from a first surface 566 of the beam splitter 558 to a beam dump 567 on a different side of the beam splitter 558 from which the light 560 originated. The second beam 562 is reflected from the first surface 566 of the beam splitter 558, to a second surface 568 of the beam splitter, to a reverse side 569 of the first surface 566 of the beam splitter. The reverse side 569 of the first surface 566 of the beam splitter 558 directs the second beam 562 to an image sensor 570 via a lens 572. Similar to the discussion above, directing the first beam 562 away from the lens 572 and the image sensor 570 may reduce reflections and/or scattering of light inside of the device or accessory in which the beam splitter 558 and the image sensor 570 are housed.

Although not explicitly pictured, other beam splitter configurations may be used in any of the described devices as well. For instance, a device may include a cube beam splitter comprised of prisms with a resin or cement layer in the interface(s) between the prisms. The resin or cement layer may be thin (e.g., 0.1 micron to 1 millimeter), which may minimize boresight offset of the cube beam splitter. A cube beam splitter may be employed in finite and/or infinite conjugate applications.

Additionally or alternatively, a beam splitter with a geometrically-patterned coating may be used in any of the described devices. The geometrically-patterned coating may reflect light in the coated area of the beam splitter, and allow light to transmit through the uncoated area of the beam splitter. An example of a beam splitter with a geometrically-patterned coating is a polka-dot beam splitter.

In some examples, a prism may be used as a beam splitter in any of the described devices. One such example is a Wollaston prism, which consists of two orthogonal prisms made of birefringent material. A Wollaston prism splits indecent light into two (or more) beams with orthogonal polarizations. One of the beams from the Wollaston prism is directed to an image sensor, and another of the beams may be directed to a healthcare provider for direct viewing.

Figure 6:
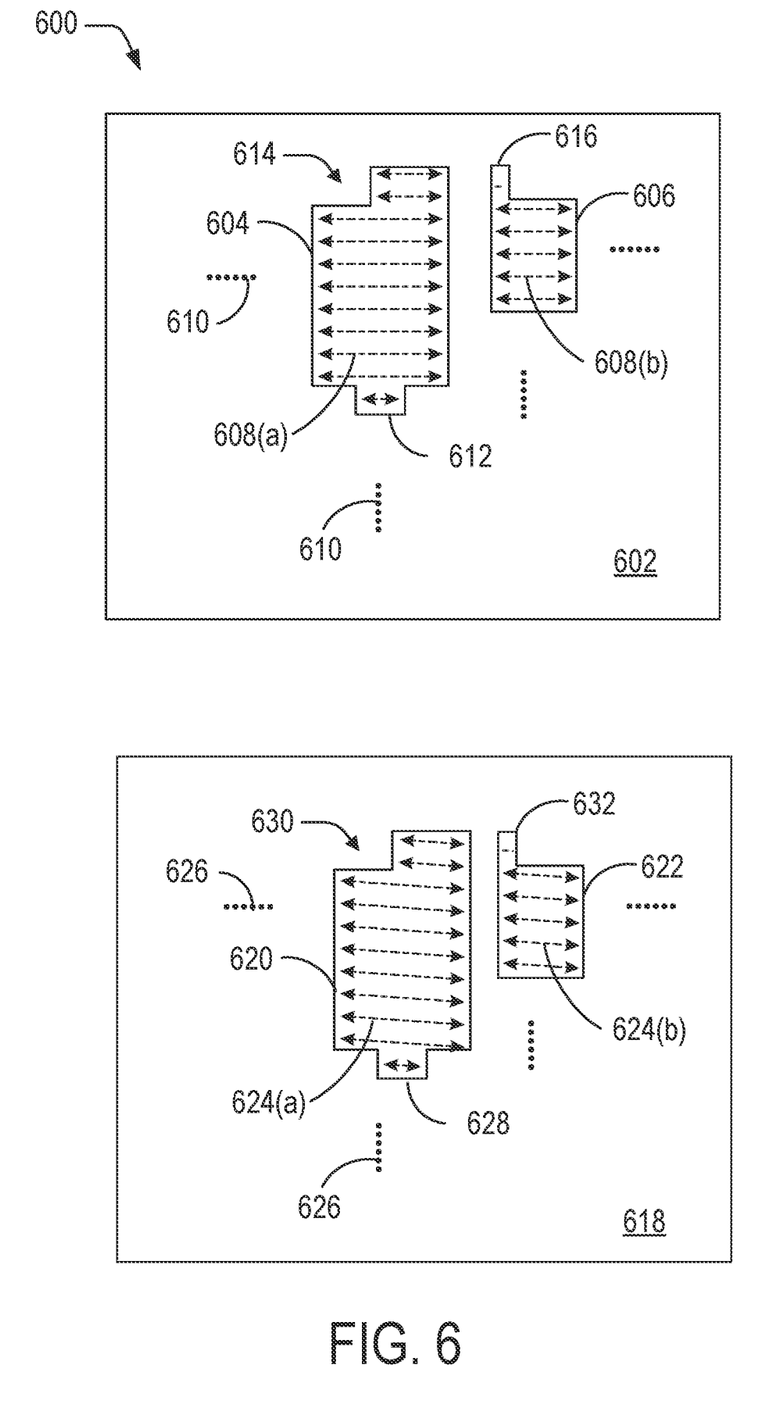
FIG. 6 illustrates configurations for polarizers to be removed from a polarized sheet that may be incorporated into a visual observation tool in accordance with examples of the present disclosure.

FIG. 6 illustrates configurations 600 for a polarizer to be removed from a polarized sheet that may be incorporated into a visual observation tool in accordance with examples of the present disclosure. In some examples, one or more polarizers may be used to reduce reflection and glare in imaging applications such as medical devices as described herein, but also in applications such as photography, machine vision, microscopy, and the like. In applications that utilize active illumination, in which lighting whose direction, intensity and pattern are controlled by commands or signals, two (or more) crossed polarizers may be used to reduce reflection and glare. The two or more crossed polarizers may be manufactured using a die cutting process, in which a machine cuts shapes out of a material (plastic, rubber, chipboard, cloth, paper, foam, sheet metal, etc.) using a specialized tool (a die) to cut the material using a press.

Polarizers maximize glare and reflection reduction when a viewing polarizer is oriented perpendicularly to the polarizing direction of the reflected light. The reflected light, in some examples, is controlled by an illumination polarizer. In some devices, the viewing polarizer and/or the illumination polarizer may be rotated to achieve the desired orientation between the two polarizers. However, many devices include built-in polarizers at fixed orientations, so performance of the polarizers is determined by the angle of tolerance in manufacturing and assembling the device that includes the polarizers. Oftentimes, manufacturing processes tolerate several degrees of deviation from a polarization axis of the polarizers to the die cutter, especially when there is no active measurement during the manufacturing process. When a device is assembled, additional deviation of the desired angle between the polarizers may be introduced by mechanical tolerance between mated parts of the device. The compounded effect of such tolerances results in glare and/or reflection in images generated by the device, and/or in direct viewing through a device. Consequently, image contrast and quality are sacrificed.

The described techniques remedy the deficiencies of conventional polarizer manufacturing processes by cutting a viewing polarizer and an illumination polarizer from a same sheet using a die cutter. In some examples, a viewing polarizer and/or accompanying illumination polarizer are cut to have a unique shape and/or tab to fit into mating features of a mechanical holder of a device, such that the polarizers fit in a desired orientation but do not fit into the device in other orientations. Orienting the viewing polarizer and the illumination polarizer inside of the device based on the mating features ensures that the light is polarized by the polarizers correctly to minimize or eliminate glare and reflections, even if there is misalignment between the polarizer sheet and the die cutter. For instance, if the polarizer sheet is misaligned from the die cutter, both the viewing polarizer and the illumination polarizer will be misaligned by the same amount, and the misalignment of both will be canceled out when inserted into the device.

To illustrate, a polarizer sheet 602 includes an illumination polarizer 604 and a viewing polarizer 606 which are to be cut from the polarizer sheet 602 by a die cutter. The illumination polarizer 604 includes lines 608(a) corresponding to a polarization direction of the polarizer sheet 602. Additionally, the viewing polarizer 606 includes lines 608(b) corresponding to the polarization direction of the polarizer sheet 602. The lines 608(a) and the lines 608(b) (collectively, lines 608) are in a same direction for both the illumination polarizer 604 and the viewing polarizer 606. The lines 608 are also substantially parallel or perpendicular to lines 610, which correspond to an orientation of the die cutter.

The illumination polarizer 604 also includes at least a tab 612 and a notch 614 that are used to orient the illumination polarizer 604 inside of a device in a desired orientation, and prevent the illumination polarizer 604 from being installed in the device in another orientation than the desired orientation. Similarly, the viewing polarizer 606 includes a tab 616 which may be used to orient the viewing polarizer 606 inside of the device in a desired orientation as well. When the illumination polarizer 604 and the viewing polarizer 606 are oriented in the device in the desired orientations using the tabs 612 and 616 and the notch 614, the lines 608(a) are perpendicular to the lines 608(b), thus polarizing light entering the device.

A polarizer sheet 618 also includes an illumination polarizer 620 and a viewing polarizer 622 which are to be cut from the polarizer sheet 618 by a die cutter. The illumination polarizer 620 includes lines 624(a) corresponding to a polarization direction of the polarizer sheet 618. Additionally, the viewing polarizer 622 includes lines 624(b) corresponding to the polarization direction of the polarizer sheet 618. The lines 624(a) and the lines 624(b) (collectively, lines 624) are in a same direction for both the illumination polarizer 620 and the viewing polarizer 622. However, the lines 624 are not, in this case, substantially parallel or perpendicular to lines 626, which correspond to an orientation of the die cutter. As noted above, the polarizer sheet 618 may be misaligned from the die cutter during manufacture of the illumination polarizer 620 and the viewing polarizer 622.

However, the misalignment may be resolved by cutting the illumination polarizer 620 and the viewing polarizer 622 from the same polarizer sheet 618, and using shapes of the illumination polarizer 620 and the viewing polarizer 622 to correctly orient these polarizers inside of a device. For instance, the illumination polarizer 620 includes at least a tab 628 and a notch 630 that are used to orient the illumination polarizer 620 inside of a device in a desired orientation, and prevent the illumination polarizer 620 from being installed in the device in another orientation than the desired orientation. Similarly, the viewing polarizer 622 includes a tab 632 which may be used to orient the viewing polarizer 622 inside of the device in a desired orientation as well. When the illumination polarizer 620 and the viewing polarizer 622 are oriented in the device in the desired orientations using the tabs 628 and 632 and the notch 630, the lines 624(a) are still perpendicular to the lines 624(b), regardless of the misalignment of the die cutter relative to the polarizer sheet 618. Accordingly, light entering the device is still polarized to correct glare and reflections, despite such misalignment.

Figure 7:
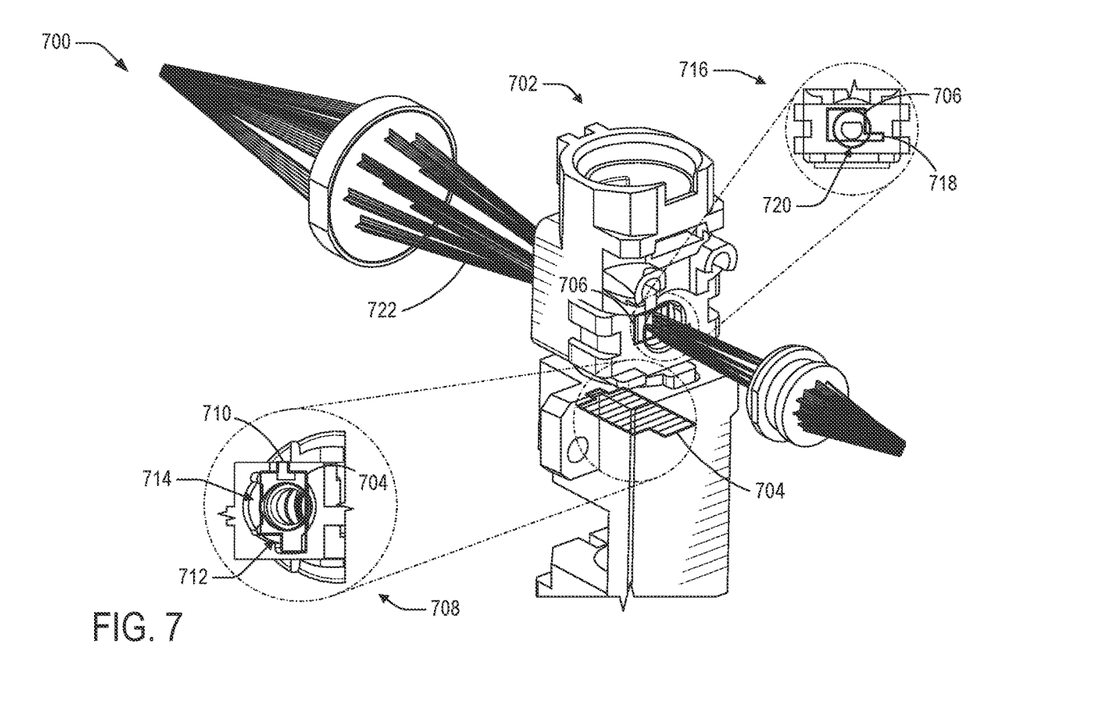
FIG. 7 illustrates a cross-sectional view of a portion of an example visual observation tool incorporating a polarizer according to the present disclosure.

FIG. 7 illustrates a cross-sectional view 700 of a portion of an example visual observation tool incorporating polarizers according to the present disclosure. The cross-sectional view 700 illustrates an ophthalmoscope 702 that has incorporated polarizers, but any medical device, microscope, camera, machine vision tool, or other device may incorporate the described techniques without departing from the scope of the disclosure. The ophthalmoscope 702 includes an illumination polarizer 704 and a viewing polarizer 706, similar to the discussion above in relation to FIG. 6.

A pop-out view 708 illustrates an orientation of the illumination polarizer 704 inside of the ophthalmoscope 702. The illumination polarizer 704 includes a tab 710 which may correspond to the tab 612 and/or the tab 618 of FIG. 6. The illumination polarizer 704 also includes and a notch 712, which may correspond to the notch 614 and/or the notch 630 of FIG. 6. The tab 710 and the notch 712 provide a shape for the illumination polarizer 704 that ensures that the illumination polarizer 704 is oriented correctly inside an opening 714 of the ophthalmoscope 702, and is prevented from being installed in another orientation other than the correct orientation.

Additionally, a pop-out view 716 illustrates an orientation of the viewing polarizer 706 inside of the ophthalmoscope 702. The viewing polarizer 706 includes a tab 718 which may correspond to the tab 616 and/or the tab 632 of FIG. 6. The tab 718 provides a shape for the viewing polarizer 706 that ensures that the viewing polarizer 706 is oriented correctly inside an opening 720 of the ophthalmoscope 702, and is prevented from being installed in another orientation other than the correct orientation. Further, the orientations of the illumination polarizer 704 and the viewing polarizer 706 based on the shapes of the polarizers, in combination with being cut from a same polarizer sheet as described in relation to FIG. 6, ensures that light 722 entering the ophthalmoscope 702 is polarized to reduce or eliminate reflections and glare.

Figure 8:
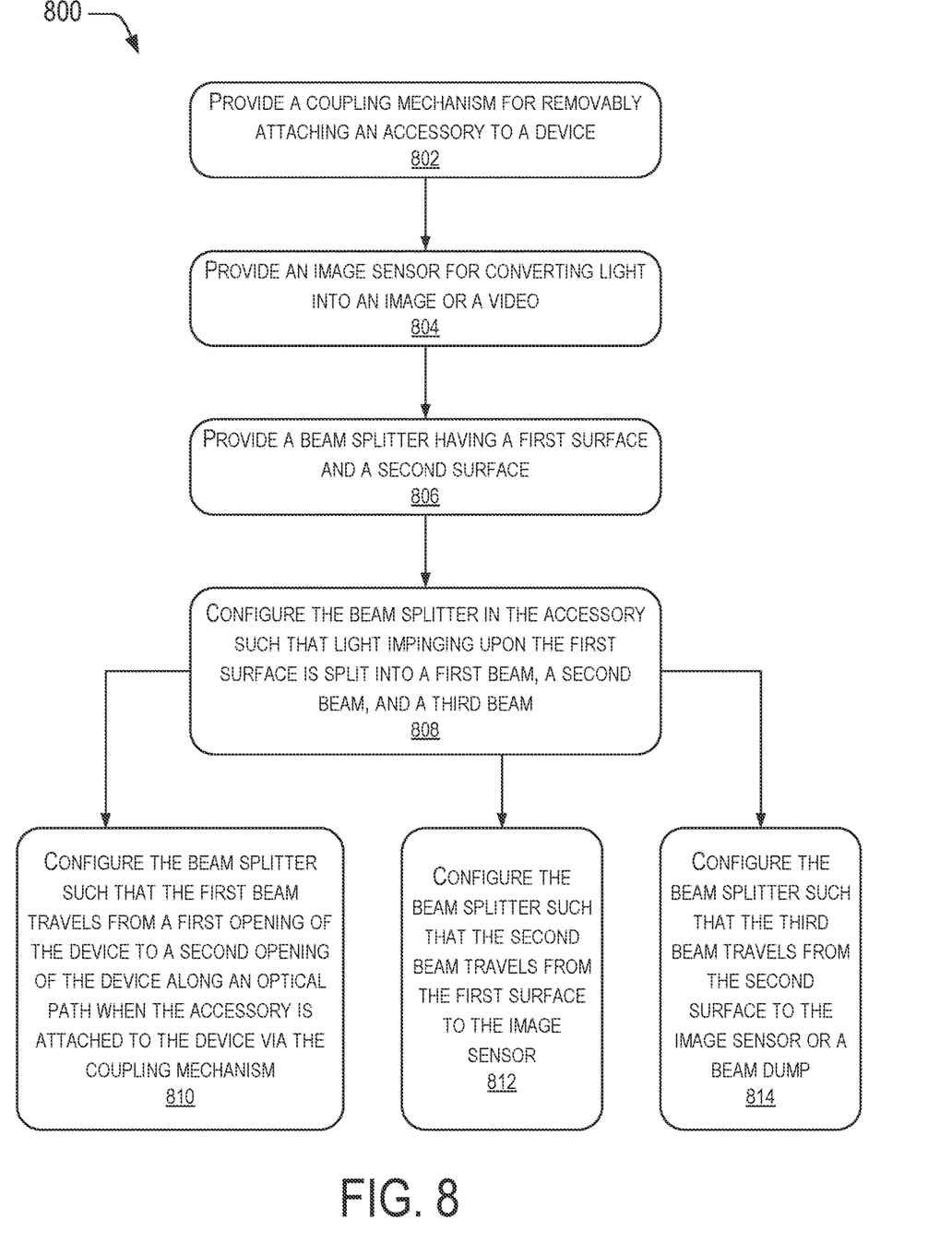
FIG. 8 illustrates a flowchart outlining an example method of manufacturing an accessory for a visual observation tool in accordance with the present disclosure.

FIG. 8 illustrates a flowchart outlining an example method 800 of manufacturing an accessory for a visual observation tool in accordance with the present disclosure. In some examples, the method 800 may be performed by one or more computing devices configured to manufacture visual observation tools. Reference will be made throughout the discussion of the method 800 to FIGS. 2, 3, 4, and 5, which show schematic illustrations of visual observation tools and/or beam splitters.

At operation 802, the method of manufacture includes providing a coupling mechanism for removably attaching an accessory 204 and/or an accessory 304 to a device, such as an otoscope 202, and ophthalmoscope 302, a dermatoscope, or other type of device. For example, the coupling mechanism may be a threaded fastener, a buckle, a clamp, a clasp, a hook and loop fastener, a latch, a pin, a snap fastener, or the like.

At operation 804, the method of manufacture includes providing an image sensor, such as the image sensor 224 and/or the image sensor 326, for converting variable attenuation of light waves into signals as the light waves pass through and/or reflect off of objects. The image sensor generates an image or a video from the signals converted from the light waves. For instance, the image sensor 224 is included in the accessory 204. The image sensor 224 may be in communication with the controller 234 comprising an image processor configured to receive signals and/or other inputs from the image sensor 224, and use the signals from the image sensor 224 to form a visual image or video of the patient 106 based on the signal.

At operation 806, the method of manufacture includes providing a beam splitter, such as the beam splitter 222 and/or the beam splitter 324, where the beam splitter has a first surface and a second surface. The beam splitter 222 and/or the beam splitter 324 may take any one of a variety of configurations, such as the parallel plate configurations 402, 420, 438, and/or 456 described in relation to FIG. 4, the wedge plate configurations 502, 520, 538, and/or 556 described in relation to FIG. 5, a cube beam splitter, a beam splitter having a geometric coating, a prism, or the like.

At operation 808, the method of manufacture includes configuring the beam splitter 222 in the accessory 204 such that light impinging upon the first surface is split into a first beam 226, a second beam 228, and a third beam (e.g., see FIGS. 4 and 5). At operation 810, the method of manufacture includes configuring the beam splitter 222 in the accessory 204 such that the first beam 226 travels from a first opening 214 of the device to a second opening 216 of the device along an optical path 218 when the accessory 204 is attached to the device via the coupling mechanism. Configuring the beam splitter 222 in this way enables the healthcare provider 104 to perform a manual examination of the patient by viewing through the device.

At operation 812, the method of manufacture includes configuring the beam splitter 222 in the accessory 204 such that the second beam 228 travels from the first surface of the beam splitter 222 to the image sensor 224. Additionally, at operation 814, the method of manufacture includes configuring the beam splitter 222 in the accessory 204 such that the third beam travels from the second surface of the beam splitter 222 to the image sensor 224 or a beam dump. For instance, the beam splitter 222 may be configured to direct the third beam to the image sensor 224 to reduce or eliminate visual effects in digital images or video such as ghosting or chromatic aberration. Alternatively or additionally, the beam splitter 222 may be configured to direct the third beam to a beam dump (e.g., see FIGS. 4 and 5) to reduce reflections and/or scattering of light in the internal space 207.

The described optical configurations enable a healthcare provider to utilize an accessory with a medical device to capture images and/or video of an exam of a patient while performing the exam using manual techniques that the healthcare provider is accustomed to. In this way, the healthcare provider can make precise measurements and/or movements with the medical device during exams of a patient's eyes, ears, and other body parts using the medical device, and capture images and/or video during the exam for later reference or real time viewing by others (e.g., a nurse or medical student).

Other embodiments of the present disclosure will be apparent to those skilled in the art from consideration of the specification and practice of the embodiments described herein. It is intended that the specification and examples be considered as example only, with a true scope and spirit of the present disclosure being indicated by the following claims.

What is claimed is:
1. A device, comprising:
a housing defining an internal space, and including a first opening and a second opening;
an optics assembly disposed within the internal space and including a collimating lens fixedly coupled to the housing, the optics assembly configured to:
receive light, via the first opening, from a source external to the housing,
collimate the light, received via the first opening, with the collimating lens, and
direct the light to pass, through the housing, to the second opening; and
an accessory removably attached to the housing, the accessory comprising:
an image sensor,
a lens configured to direct light to the image sensor, and
a beam splitter having a first surface and a second surface, the accessory being configured such that when the accessory is removably attached to the housing:
the beam splitter is positioned within the housing such that the light collimated by the collimating lens impinges upon the first surface, and
the beam splitter splits the light impinging upon the first surface into at least a first beam, a second beam, and a third beam, such that:
the first beam is directed from the first surface to the second opening along a first optical path extending from the first surface to the second opening,
the second beam is directed, from the first surface to the image sensor, along a second optical path, the second beam passing from the first surface to the lens of the accessory without passing through additional optical components, and the third beam is directed, from the first surface to the image sensor or a beam dump, along a third optical path extending from the first surface to the image sensor or the beam dump via the second surface, wherein:
directing the third beam to the image sensor along the third optical path includes directing the third beam from the second surface of the beam splitter, through the lens of the accessory, and to the image sensor such that:
the third beam converges and overlaps with the second beam on the image sensor, and
at least one of ghosting and chromatic aberration is eliminated in an image formed by the image sensor using the second beam and the third beam.

2. The device of claim 1, wherein the device is an otoscope, ophthalmoscope, or a dermatoscope, and directing the third beam to the beam dump along the third optical path includes directing the third beam from the second surface of the beam splitter away from the image sensor such that:
the third beam avoids impinging upon the image sensor, and
at least one of ghosting and chromatic aberration is eliminated in an image formed by the image sensor without using the third beam.

3. The device of claim 1, wherein the image sensor converts the at least the second beam to an image or a video of at least a portion of a patient adjacent the first opening.

4. The device of claim 1, wherein the accessory further comprises:
a digital storage component in communication with the image sensor, the digital storage component configured to store an image or a video captured by the image sensor; and
a digital transfer component configured to transfer the image or the video from the digital storage component to a remote computing device.

5. The device of claim 1, wherein the beam splitter comprises an uncoated substrate.

6. The device of claim 1, wherein the first surface of the beam splitter is substantially parallel to the second surface of the beam splitter.

7. The device of claim 1, wherein directing the third beam to the imaging sensor along the third optical path further includes converging the second beam and the third beam with the lens of the accessory such that the at least one of ghosting and chromatic aberration is eliminated.

8. The device of claim 1, wherein the beam splitter comprises a wedge plate, a cube, a prism, or a geometric coating disposed on a substantially transparent substrate.

9. The device of claim 1, wherein a thickness of the beam splitter extending from the first surface of the beam splitter to the second surface of the beam splitter has a value between approximately 1 micron and approximately 50 millimeters.

10. An accessory attachable to a housing of a medical device, the accessory comprising:
an image sensor;
a first lens configured to direct light to the image sensor; and
a beam splitter having a first surface and a second surface, wherein when the accessory is attached to the housing of the medical device,
the beam splitter is positioned within the housing such that light, entering the housing via a first opening of the housing and collimated by a second lens fixedly coupled to the housing, impinges upon the first surface of the beam splitter, and
the beam splitter is configured to split the light into at least a first beam, a second beam, and a third beam, such that:
the first beam is directed, from the first surface to a second opening of the housing, along a first optical path extending from the first surface to the second opening,
the second beam is directed, from the first surface to the image sensor, along a second optical path, the second beam passing from the first surface to the first lens without passing through additional optical components, and
the third beam is directed, from the first surface to the image sensor or a beam dump, along a third optical path extending from the first surface to the image sensor or the beam dump via the second surface, wherein:
directing the third beam to the image sensor along the third optical path includes directing the third beam from the second surface of the beam splitter, through the first lens, and to the image sensor such that:
the third beam converges and overlaps with the second beam on the image sensor, and
at least one of ghosting and chromatic aberration is eliminated in an image formed by the image sensor using the second beam and the third beam.

11. The accessory of claim 10, wherein the medical device comprises an otoscope, ophthalmoscope, or a dermatoscope, and directing the third beam to the beam dump along the third optical path includes directing the third beam from the second surface of the beam splitter away from the image sensor such that:
the third beam avoids impinging upon the image sensor, and
at least one of ghosting and chromatic aberration is eliminated in an image formed by the image sensor without using the third beam.

12. The accessory of claim 10, further comprising:
a digital storage component in communication with the image sensor, the digital storage component configured to store an image or a video captured by the image sensor; and
a digital transfer component configured to transfer the image or the video from the digital storage component to a remote computing device.

13. The accessory of claim 10, wherein the beam splitter comprises an uncoated substrate.

14. The accessory of claim 10, wherein the first surface of the beam splitter is substantially parallel to the second surface of the beam splitter.

15. The accessory of claim 10, wherein the beam splitter comprises a wedge plate, a cube, a prism, or a geometric coating disposed on a substantially transparent substrate.

16. A method of manufacturing an accessory for a medical device, comprising:
providing a coupling mechanism for removably attaching the accessory to the medical device;
providing an image sensor for converting light into an image or a video;
providing a beam splitter having a first surface and a second surface;

providing a first lens configured to direct light from the beam splitter to the image sensor, wherein when the accessory is attached to the housing of the medical device,
- the beam splitter is positioned within the housing such that light, entering the housing via a first opening of the housing and collimated by a second lens fixedly coupled to the housing, impinges upon the first surface of the beam splitter, and
- the beam splitter is configured to split the light into at least a first beam, a second beam, and a third beam, such that:
  - the first beam is directed, from the first surface to a second opening of the housing, along a first optical path extending from the first surface to the second opening when the accessory is attached to the medical device via the coupling mechanism,
  - the second beam is directed, from the first surface to the image sensor, along a second optical path, the second beam passing from the first surface to the first lens without passing through additional optical components, and
  - the third beam is directed, from the first surface to the image sensor or a beam dump, along a third optical path extending from the first surface to the image sensor or the beam dump via the second surface, wherein:
    - directing the third beam to the image sensor along the third optical path includes directing the third beam from the second surface of the beam splitter, through the first lens, and to the image sensor such that:
      - the third beam converges and overlaps with the second beam on the image sensor, and
      - at least one of ghosting and chromatic aberration is eliminated in an image formed by the image sensor using the second beam and the third beam.

17. The method of claim 16, wherein the medical device is an otoscope, ophthalmoscope, or a dermatoscope, and directing the third beam to the beam dump along the third optical path includes directing the third beam from the second surface of the beam splitter away from the image sensor such that:
- the third beam avoids impinging upon the image sensor, and
- at least one of ghosting and chromatic aberration is eliminated in an image formed by the image sensor without using the third beam.

18. The method of claim 16, further comprising:
- providing a digital storage component in communication with the image sensor, the digital storage component configured to store an image or a video captured by the image sensor; and
- providing a digital transfer component configured to transfer the image or the video from the digital storage component to a remote computing device.

19. The method of claim 16, wherein directing the third beam to the imaging sensor along the third optical path further includes converging the second beam and the third beam with the first lens such that the at least one of ghosting and chromatic aberration is eliminated.

20. The method of claim 16, wherein a thickness of the beam splitter extending from the first surface of the beam splitter to the second surface of the beam splitter has a value between approximately 1 micron and approximately 50 millimeters.

* * * * *